United States Patent [19]

Moy

[11] 4,356,328
[45] Oct. 26, 1982

[54] PROCESS FOR THE PREPARATION OF ACETALDEHYDE

[75] Inventor: David Moy, Ridgewood, N.J.

[73] Assignee: The Halcon SD Group, Inc., New York, N.Y.

[21] Appl. No.: 194,324

[22] Filed: Oct. 6, 1980

[51] Int. Cl.³ .............................................. C07C 47/06
[52] U.S. Cl. .................................... 568/484; 568/485; 568/486; 568/488; 568/489
[58] Field of Search ............... 568/484, 485, 486, 488, 568/489

[56] References Cited

U.S. PATENT DOCUMENTS

| | | | |
|---|---|---|---|
| 2,727,902 | 12/1955 | Reppe et al. | 568/485 |
| 3,285,948 | 11/1966 | Butter | 568/485 |
| 3,356,734 | 12/1967 | Kuraishi et al. | 568/485 |
| 3,531,531 | 9/1970 | Copelin | 568/484 |
| 3,579,566 | 5/1971 | Fenton | 568/485 |
| 3,631,188 | 12/1971 | Wakamatsu | 568/484 |

*Primary Examiner*—Werren B. Lone
*Attorney, Agent, or Firm*—William C. Long; Riggs T. Stewart; Harold N. Wells

[57] ABSTRACT

Acetaldehyde is produced by reacting acetic anhydride with hydrogen in the presence of a supported Group VIII noble metal catalyst wherein the reaction is carried out in the liquid phase.

4 Claims, No Drawings

PROCESS FOR THE PREPARATION OF ACETALDEHYDE

This invention relates to the preparation of acetaldehyde and is more particularly concerned with the preparation of acetaldehyde by conversion of acetic anhydride.

Acetaldehyde is a well-known chemical of commerce, used primarily as an intermediate in the production of organic chemicals, and has been produced commercially for many years, for example by the hydration of acetylene and the catalytic oxidation of ethyl alcohol, ethylene and saturated hydrocarbons such as butane. More recently it has been discovered that acetaldehyde can be produced by the action of carbon monoxide and hydrogen upon alcohols, ethers and esters in the presence of catalysts based on metals of the 8th Group of the Periodic Table. Such reactions are described, for example, in Reppe et al. U.S. Pat. No. 2,727,902, Butter U.S. Pat. No. 3,285,948, Kuraishi et al. U.S. Pat. No. 3,356,734, and Japanese Patent publication 48-19286, and require the use of very high superatmospheric pressures. Belgian Pat. No. 839,321, which is the counterpart of U.S. application Ser. No. 654,662 filed Feb. 5, 1976, discloses the preparation of acetaldehyde as a by-product in the manufacture of ethylidene diacetate by reacting carbon monoxide and hydrogen with methyl acetate at moderate superatmospheric pressures. The selectivity to acetaldehyde described in these publications is, however, in general relatively low and this is obviously a disadvantage when acetaldehyde is the desired product. Fenton U.S. Pat. No. 3,579,566 treats organic acid anhydrides such as acetic anhydride with hydrogen in the presence of a catalyst comprising a complex of a Group VIII noble metal with a biphyllic ligand from the group consisting of trihydrocarbyl phosphines, arsines and stibines. The Fenton examples show the preparation primarily of ethylidene diacetate from acetic anhydride by this technique. Small amounts of acetaldehyde are also reported by Fenton but the amounts produced are inadequate when it is desired to have acetaldehyde as the principal product along with acetic acid. Belgian Pat. No. 879,178 converts anhydrides to 1,1-diesters with hydrogen in the presence of certain supported metals, including metals of Group VIII of the Periodic Table, and in the presence of a strong protonic acid such as hydrochloric and hydrofluoric acids. No formation of acetaldehyde is shown.

It is, therefore, an object of this invention to provide a process for the preparation of acetaldehyde in which the selectivity to acetaldehyde is significantly increased and in which the reaction can be carried out at moderately elevated pressures.

In accordance with this invention, this and other objects are realized by continuously reacting acetic anhydride with hydrogen in the presence of a Group VIII noble metal catalyst with the reaction being carried out in the vapor phase and the catalyst being supported, i.e., being carried on a support or carrier. A vapor phase reaction is, of course, one in which the reactants and the reaction products are essentially all in the vapor phase at all times and the catalyst is in the form of a non-vaporized solid over which the reactants are passed. It has been surprisingly discovered that when a Group VIII noble metal catalyst, especially palladium, rhodium, ruthenium and platinum, particularly palladium, is employed, and the reaction is carried out under vapor-phase conditions of the character described, the selectivity to acetaldehyde is significantly increased and can approach its theoretical maximum.

The reaction of hydrogen upon acetic anhydride to produce acetaldehyde can be illustrated by the following equation:

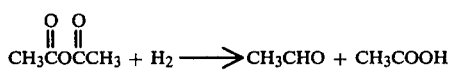

As will be seen from the foregoing equation, one mol of acetic anhydride will theoretically produce a mol of acetaldehyde and a mol of acetic acid. In accordance with the invention, the formation of other products, such as ethylidene diacetate, which tend to reduce the yield of acetaldehyde is minimized so that the quantity of acetaldehyde produced from a unit quantity of acetic anhydride will more nearly approach the theoretical. At the same time, the amount of acetic anhydride converted to acetaldehyde and acetic acid is maintained at a desirable level. The term "selectivity" as used herein has its conventional meaning viz.

$$\% \text{ selectivity} = \frac{\text{mols acetaldehyde produced}}{\text{mols acetic anhydride reacted}} \times 100$$

As will be seen from the equation set forth above, the theoretical selectivity to acetaldehyde is 100% when one mol of acetaldehyde and one mol of acetic acid are produced per mol of acetic anhydride reacted.

It has been found that the mol ratio of hydrogen to acetic anhydride in the feed to the vapor-phase reaction zone has an influence on the production of acetaldehyde in relation to the production of products by competing reactions, such as the production of ethylidene diacetate by the following reaction:

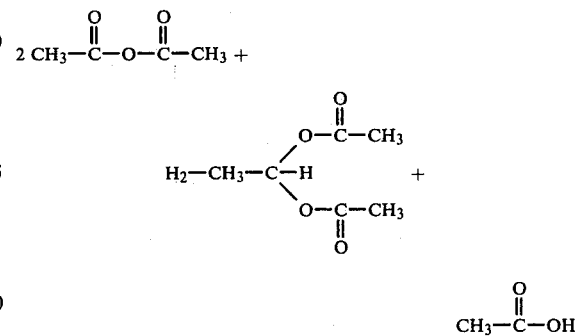

It is preferred, therefore, that the mol ratio of hydrogen to acetic anhydride be at least 5:1. Operation at lower ratios can, however, be carried out since acetaldehyde is still produced in substantial amounts, but ordinarily the ratio is suitably at least 1:1. The upper limit is governed only by economic considerations. Preferably the mol ratio of hydrogen to acetic anhydride is at most 100:1, most preferably 50:1.

The Group VIII noble metal catalyst is supplied and used in supported form, i.e., carried on or dispersed on a support or carrier which is of such size that it can be employed in fixed or fluidized bed reactors, e.g., from 400 mesh/inch to ½-inch particle sizes. The range of variation of the pore volume relative to solid weight is from 0.03 to 2.5 cm³/gram of the porous phase, with a preferred range of from 0.05 to 1.5 cm³/gram.

Conventional carrier materials can be used, as exemplified by pumice, alumina, silica, silica-alumina, aged or deactivated silica-alumina cracking catalyst, magnesia, diatomaceous earth, bauxite, titania, zirconia, clays, both natural and acid treated such as Super-Filtrols, attapulgus clay (attapulgite), lime, magnesium silicate, silicon carbide, activated and unactivated carbons, zeolites as well as the zeolitic molecular sieves, solid foams, such as ceramic honeycombs, and porous organic polymers. The above carriers are used as regular and irregular particles and as capillary tubes, and interspacing elements such as shapes, extrudates, ceramic rods, balls, broken pieces, tiles, and the like, disposed within the reactor.

The catalyst component can be applied to the carrier in conventional manner, e.g., by impregnation of the carrier with a solution of a soluble compound of the Group VIII noble metal, e.g., a halide, nitrate or the like, followed by drying. If desired, the catalyst can be pre-activated, for example, by heating it in the presence of hydrogen. Catalyst component concentration upon the carrier may vary widely, e.g., 0.01 weight percent to 10 weight percent, or higher.

The hydrogen is preferably employed in substantially pure form as available commercially, but inert diluents such as nitrogen, methane, and noble gases can be present if desired. The presence of inert diluents does not affect the reaction but their presence makes it necessary to increase the total pressure in order to maintain the desired hydrogen partial pressure. The hydrogen is preferably substantially free of CO. The hydrogen should also be essentially dry, i.e., the hydrogen and the other reactants should be reasonably free from water. The presence of minor amounts of water such as may be found in the commercial forms of the reactants is, however, entirely acceptable.

The temperature of the reaction mixture is selected to keep the reactants and the reaction products continuously in the vapor-phase as they pass over the catalyst bed in the vapor-phase reactor at the total pressure and total gas flow rate employed. Ordinarily, the temperature will lie within the range of 140° and 225° C. Higher temperatures can be employed but there is no particular advantage in their use. The time of reaction is not a parameter of the process and depends largely upon the temperature employed, but typical volume space velocities, by way of example, will generally fall in the range of 500 to 10,000 hr.$^{-1}$.

The reaction is carried out under superatmospheric pressure but excessively high pressures, which require special high-pressure equipment, are not necessary. In general, the reaction is effectively carried out by employing a hydrogen partial pressure which is preferably 30 to 3,000 psi, although a hydrogen partial pressure within the broader range of 10 to 10,000 psi can also be employed. The total pressure is that required to provide the desired hydrogen partial pressure and to maintain the vapor phase. Typically, up to about 3,500 psig are used. The reaction can be advantageously carried out in a conventional fluid-bed or fixed-bed reactor.

It will be apparent that the reactions referred to above are carried out under substantially anhydrous conditions. The presence of minor amounts of water, however, such as may be found in commercially available reactants, is permissible. Normally, however, the presence of more than 5 mol % of water in any one or more of the reactants should be avoided, the presence of less than 3 mol % of water desired, and the presence of less than 1 mol % is preferred.

The effluent from the reaction zone is entirely gaseous, i.e., it is composed of the non-condensible gases in the reaction system, e.g., hydrogen, as well as vaporized organic compounds including the product acetaldehyde, unreacted acetic anhydride, and acetic acid.

The vaporous reaction mixture is continuously removed from the reaction zone and partially condensed to separate the higher boiling constituents and to provide a net product consisting of acetaldehyde which is then separately condensed or otherwise recovered, to remove it from the non-condensible gas component, e.g., hydrogen. In the above-described reaction in which the reactants, e.g., acetic anhydride and hydrogen, are continuously supplied to the reaction zone, after removal of acetaldehyde as above-described, the other components of the vapor effluent, both gaseous and liquid, particularly unreacted acetic anhydride and hydrogen, can be continuously recycled to the reaction zone. The Group VIII noble metal catalyst remains in the reaction zone at all times and only the vaporous effluent is removed. A purge of the recycled gases may be taken in conventional manner to prevent the build-up of contaminating gases which may have been present in the hydrogen feed to the system such as nitrogen or may have been produced in the reaction itself.

The following examples will serve to provide a fuller understanding of the invention, but it is to be understood that they are given for illustrative purposes only, and are not to be construed as limitative of the invention. In the examples, percentages are on a molar basis, unless otherwise indicated.

EXAMPLE 1

A reactor is used which is in the form of a one ft. tube having an internal diameter of ⅜ in. and provided with a temperature controller, a thermocouple, a pressure controller, a preheater, a feed inlet and a gas outlet leading to a series of condensers. The reactor tube is filled to a depth of 5 in. with 20 cc. (19 grams) of palladium supported (5 wt. %) on ⅛" pellets of alumina. Hydrogen and vaporized acetic anhydride (premixed and vaporized in the preheater) are passed into the reactor for 2 hours at a temperature of 185° C. at a total pressure of 100 psig and a hydrogen partial pressure of 110 psi at the rate of 12.5 cc. per hour of acetic anhydride and 77 liters per hour of hydrogen, and a volume space velocity of about 4,000 hr.$^{-1}$ Gas chromatographic (G.C.) analysis of the vaporous effluent after condensation shows a selectivity to acetaldehyde of 79% and an acetaldehyde to acetic acid ratio of 1. No ethylidene diacetate is detected.

EXAMPLE 2

Example 1 is repeated with the exception that the pressure is maintained at 60 psig and the effluent vapors exiting from the condensers are passed through a scrubber at −80° C. containing a liquid for absorbing additional acetaldehyde, i-propyl alcohol in this case but other liquids such as ethylbenzene, ethyl alcohol, acetone and the like can be used. Selectivity to acetaldehyde is found to be 85% and the acetaldehyde to acetic acid ratio is 0.84. No ethylidene diacetate is detected.

EXAMPLE 3

Example 2 is repeated but the hydrogen feed rate is changed to 27 liters per hour. Analysis shows a selectivity to acetaldehyde of 81% and an acetaldehyde to acetic acid ratio of 0.91. Ethylidene diacetate is detected representing a selectivity to this compound of 1.2%.

EXAMPLE 4

Example 3 is repeated except that the pressure is further reduced to 30 psig. Analysis shows a 76% selectivity to acetaldehydeand an acetaldehyde to acetic acid ratio of 0.71. No ethylidene diacetate is detected.

EXAMPLE 5

Example 2 is repeated but at a temperature of 160° C. Analysis shows a selectivity to acetaldehyde of 96% and an acetaldehyde to acetic acid ratio of 0.94. Only a trace of ethylidene diacetate is detected.

EXAMPLE 6

Example 2 is again repeated at a temperature of 150° C., a pressure of 60 psig, an acetic anhydride feed rate of 13.4 cc. per hour and a hydrogen feed rate of 77 liters per hour, the process being carried out for 4 hours. Analysis shows a selectivity to acetaldehyde of 99% and an acetaldehyde to acetic acid ratio of 0.99. No ethylidene diacetate is detected.

EXAMPLE 7

Example 7 is repeated at a pressure of 100 psig, an acetic anhydride feed rate of 13.7 cc. per hour and a hydrogen feed rate of 108 liters per hour, the process being carried out for 3 hours. Analysis shows a selectivity to acetaldehyde of 73% and an acetaldehyde to acetic ratio of 0.84. Only a trace of ethylidene diacetate is detected.

EXAMPLE 8

In this example, the catalyst is 20 cc. (9.2 g.) of 1% palladium on activated carbon (4×8 mesh size). Using the procedure and apparatus of Example 1 with the apparatus supplemented with a scrubber as in Example 2, reaction is carried out at a temperature of 185° C., a pressure of 30 psig, an acetic anhydride feed rate of 12.5 cc. per hour and a hydrogen feed rate of 77 liters per hour, the process being carried out for 2 hours. Analysis shows a selectivity to acetaldehyde of 93% and an acetaldehyde to acetic acid ratio of 1. Only a trace of ethylidene diacetate is detected.

EXAMPLE 9

Example 8 is repeated at a temperature of 150° C., a pressure of 30 psig, an acetic anhydride feed rate of 12.5 cc. per hour and a hydrogen feed rate of 77 liters per hour, the process being carried out for 2 hours. Analysis shows a selectivity to acetaldehyde of 86% and an acetaldehyde to acetic acid ratio of about 1. Selectivity of ethylidene diacetate is 0.6%.

EXAMPLE 10

Example 8 is again repeated at a temperature of 185° C., a pressure of 60 psig, an acetic anhydride feed rate of 12.5 cc. per hour and a hydrogen feed rate of 77 liters per hour, the process being carried out for 2 hours. Analysis shows a selectivity to acetaldehyde of 91% and an acetaldehyde to acetic acid ratio of 0.98. Selectivity to ethylidene diacetate is 0.2%.

EXAMPLE 11

Again Example 8 is repeated at a temperature of 150° C., a pressure of 60 psig, an acetic anhydride feed rate of 12.5 cc. per hour and a hydrogen feed rate of 77 liters per hour, the process being carried out for 2 hours. Analysis shows a selectivity to acetaldehyde of 83% and an acetaldehyde to acetic acid ratio of 0.93. Selectivity to ethylidene diacetate is 2%.

EXAMPLE 12

Example 8 is again repeated at a temperature of 150° C., a pressure of 60 psig, an acetic anhydride feed rate of 23.5 cc. per hour and a hydrogen feed rate of 77 liters per hour, the process being carried out for 2 hours. Analysis shows a selectivity to acetaldehyde of 91% and an acetaldehyde to acetic acid ratio of 0.98. Selectivity to ethylidene diacetate is 4.8%.

What is claimed is:

1. A process for the preparation of acetaldehyde which comprises reacting acetic anhydride with hydrogen in the presence of a supported Group VIII noble metal catalyst wherein the reaction is carried out in the vapor phase, whereby acetaldehyde is produced with high selectivity and the formation of ethylidene diacetate is minimized.

2. A process as defined in claim 1, wherein the reaction is carried out under a temperature of 140°–225° C. and under a partial pressure of hydrogen of 30–3,000 psi.

3. A process as defined in claim 1, wherein the Group VIII noble metal is palladium.

4. A process as defined in claim 3, wherein the palladium catalyst is palladium in zero valent state on an alumina support.

* * * * *

UNITED STATES PATENT AND TRADEMARK OFFICE
CERTIFICATE OF CORRECTION

PATENT NO. : 4,356,328
DATED : October 26, 1982
INVENTOR(S) : David Moy

It is certified that error appears in the above-identified patent and that said Letters Patent is hereby corrected as shown below:

Add the following claims:

5. A process as defined in Claim 3, wherein the palladium catalyst is palladium in zero valent state on a silica support.

6. A process as defined in Claim 3, wherein the palladium catalyst is palladium in zero valent state on an activated carbon support.

On the title page "4 Claims" should read -- 6 Claims --.

Signed and Sealed this

Twenty-first Day of February 1984

[SEAL]

Attest:

GERALD J. MOSSINGHOFF

Attesting Officer     Commissioner of Patents and Trademarks